United States Patent
Li et al.

(10) Patent No.: US 9,951,054 B2
(45) Date of Patent: Apr. 24, 2018

(54) CMP POROUS PAD WITH PARTICLES IN A POLYMERIC MATRIX

(75) Inventors: Shoutian Li, Naperville, IL (US);
Robert Vacassy, Aurora, IL (US);
Jaishankar Kasthuri, Aurora, IL (US)

(73) Assignee: Cabot Microelectronics Corporation, Aurora, IL (US)

(*) Notice: Subject to any disclaimer, the term of this patent is extended or adjusted under 35 U.S.C. 154(b) by 1520 days.

(21) Appl. No.: 12/761,016

(22) Filed: Apr. 15, 2010

(65) Prior Publication Data
US 2010/0273399 A1 Oct. 28, 2010

Related U.S. Application Data

(60) Provisional application No. 61/214,432, filed on Apr. 23, 2009.

(51) Int. Cl.
| | | |
|---|---|---|
| B24B 1/00 | (2006.01) | |
| B24D 3/32 | (2006.01) | |
| C09K 3/14 | (2006.01) | |
| C07D 413/04 | (2006.01) | |
| C07D 235/06 | (2006.01) | |
| C07D 403/04 | (2006.01) | |
| C07D 403/14 | (2006.01) | |
| C07D 405/14 | (2006.01) | |
| C07D 413/14 | (2006.01) | |
| C07D 417/14 | (2006.01) | |
| C07D 471/04 | (2006.01) | |

(52) U.S. Cl.
CPC ......... *C07D 413/04* (2013.01); *C07D 235/06* (2013.01); *C07D 403/04* (2013.01); *C07D 403/14* (2013.01); *C07D 405/14* (2013.01); *C07D 413/14* (2013.01); *C07D 417/14* (2013.01); *C07D 471/04* (2013.01)

(58) Field of Classification Search
CPC ........ B24B 37/24; B24B 37/245; C08G 71/04
USPC .................................................. 51/296, 308
See application file for complete search history.

(56) References Cited

U.S. PATENT DOCUMENTS

| | | | | |
|---|---|---|---|---|
| 4,927,432 | A * | 5/1990 | Budinger et al. | 51/298 |
| 6,328,634 | B1 * | 12/2001 | Shen et al. | 451/41 |
| 6,477,926 | B1 * | 11/2002 | Swisher et al. | 451/526 |
| 6,659,846 | B2 * | 12/2003 | Misra et al. | 451/41 |
| 6,896,593 | B2 * | 5/2005 | Prasad | 451/41 |
| 7,195,544 | B2 | 3/2007 | Prasad | |
| 7,699,684 | B2 | 4/2010 | Prasad | |
| 2002/0004357 | A1 | 1/2002 | Baker, III et al. | |
| 2004/0166790 | A1 * | 8/2004 | Balijepalli et al. | 451/526 |

(Continued)

FOREIGN PATENT DOCUMENTS

| | | |
|---|---|---|
| JP | 2006-297497 A | 11/2006 |
| JP | 2007-531276 A | 11/2007 |

*Primary Examiner* — Shuangyi Abu Ali
(74) *Attorney, Agent, or Firm* — Thomas Omholt; Erika S. Wilson (57) ABSTRACT

The invention provides a chemical-mechanical polishing pad comprising a polymeric matrix and 0.1-15 wt. % of metal oxide particles. The polymeric matrix has pores, the metal oxide particles are uniformly distributed throughout the pores, and the metal oxide particles have a specific surface area of about 25 $m^2/g$ to about 450 $m^2/g$. The invention further provides a method of polishing a substrate with the polishing pad.

20 Claims, 3 Drawing Sheets

(56) References Cited

U.S. PATENT DOCUMENTS

2005/0215177 A1     9/2005   Prasad
2007/0180778 A1     8/2007   Prasad \* cited by examiner

CMP POROUS PAD WITH PARTICLES IN A POLYMERIC MATRIX

CROSS-REFERENCE TO RELATED APPLICATIONS

This application claims priority to provisional application Serial No. 61/214,432, filed on Apr. 23, 2009, which is incorporated herein by reference in its entirety.

FIELD OF THE INVENTION

This invention pertains to a polishing pad for chemical-mechanical polishing.

BACKGROUND OF THE INVENTION

Chemical-mechanical polishing ("CMP") processes are used in the manufacturing of microelectronic devices to form flat surfaces on semiconductor wafers, Field emission displays, and many other microelectronic substrates. For example, the manufacture of semiconductor devices generally involves the formation of various process layers, selective removal or patterning of portions of those layers, and deposition of yet additional process layers to form a semiconductor wafer. The process layers can include, by way of example, insulation layers, gate oxide layers, conductive layers, and layers of metal or glass, etc. It is generally desirable in certain steps of the wafer process that the uppermost surface of the process layers be planar, i.e., flat, for the deposition of subsequent layers. CMP is used to planarize process layers wherein a deposited material, such as a conductive or insulating material, is polished to planarize the wafer for subsequent process steps.

In a typical CMP process, a wafer is mounted upside down on a carrier in a CMP tool. A force pushes the carrier and the wafer downward toward a polishing pad. The carrier and the wafer are rotated above the rotating polishing pad on the CMP tool's polishing table. A polishing composition (also referred to as a polishing slurry) generally is introduced between the rotating wafer and the rotating polishing pad during the polishing process. The polishing composition typically contains a chemical that interacts with or dissolves portions of the uppermost wafer layer(s) and an abrasive material that physically removes portions of the layer(s). The wafer and the polishing pad can be rotated in the same direction or in opposite directions, whichever is desirable for the particular polishing process being carried out. The carrier also can oscillate across the polishing pad on the polishing table.

Polishing pads used in chemical-mechanical polishing processes are manufactured using both soft and rigid pad materials, which include polymer-impregnated fabrics, microporous films, cellular polymer foams, non-porous polymer sheets, and sintered thermoplastic particles.

A pad containing a polyurethane resin impregnated into a polyester non-woven fabric is illustrative of a polymer-impregnated fabric polishing pad. Microporous polishing pads include microporous urethane films coated onto a base material, which is often an impregnated fabric pad. These polishing pads are closed cell, porous films. Cellular polymer foam polishing pads contain a closed cell structure that is randomly and uniformly distributed in all three dimensions.

Non-porous polymer sheet polishing pads include a polishing surface made from solid polymer sheets, which have no intrinsic ability to transport slurry particles (see, for example, U.S. Pat. No. 5,489,233). These solid polishing pads are externally modified with large and/or small grooves that are cut into the surface of the pad purportedly to provide channels for the passage of slurry during chemical-mechanical polishing. Such a non-porous polymer polishing pad is disclosed in U.S. Pat. No. 6,203,407, wherein the polishing surface of the polishing pad comprises grooves that are oriented in such a way that purportedly improves selectivity in the chemical-mechanical polishing.

Also in a similar fashion, U.S. Pat. Nos. 6,022,268, 6,217,434, and 6,287,185 disclose hydrophilic polishing pads with no intrinsic ability to absorb or transport slurry particles. The polishing surface purportedly has a random surface topography including (a) microaspersities that have a dimension of 10 μm or less and are formed by solidifying the polishing surface and (b) macro defects (or macrotexture) that have a dimension of 25 μm or greater and are formed by cutting.

Sintered polishing pads comprising a porous open-celled structure can be prepared from thermoplastic polymer resins. For example, U.S. Pat. Nos. 6,062,968 and 6,126,532 disclose polishing pads with open-celled, microporous substrates, produced by sintering thermoplastic resins. The resulting polishing pads preferably have a void volume of 25-50% and a density of 0.7-0.9 g/cm$^3$. Similarly, U.S. Pat. Nos. 6,017,265, 6,106,754, and 6,231,434 disclose polishing pads with uniform, continuously interconnected pore structures, produced by sintering thermoplastic polymers at high pressures in excess of 689.5 kPa (100 psi) in a mold having the desired final pad dimensions.

Polishing pads having a microporous foam structure are commonly known in the art. For example, U.S. Pat. No. 6,454,634 discloses a porous polishing pad having a hydrolytically stable layer and optionally comprising abrasive particles. Similarly U.S. Pat. No. 7,195,544 discloses a pad comprising a polymeric material having pores and a component dispersed within the pores. U.S. Patent Application Publication 2006/0046622 discloses a polishing pad comprising a porous polymeric material comprising two or more adjacent regions having non-zero void volumes.

Although several of the above-described polishing pads are suitable for their intended purpose, a need remains for other polishing pads that provide effective planarization, particularly in the chemical-mechanical polishing of a substrate. In addition, there is a need for polishing pads having satisfactory features such as polishing efficiency, low defectivity, and polishing uniformity. The invention provides such a polishing pad. These and other advantages of the invention, as well as additional inventive features, will be apparent from the description of the invention provided herein.

BRIEF SUMMARY OF THE INVENTION

The invention is directed to a chemical-mechanical polishing pad comprising a polymeric matrix and 0.1-15 wt. % of metal oxide particles, wherein the polymeric matrix has pores, the metal oxide particles are uniformly distributed throughout the pores, and the metal oxide particles have a specific surface area of about 25 m$^2$/g to about 450 m$^2$/g.

The invention further provides a method of polishing a substrate comprising (a) providing a polishing pad having a polishing layer comprised of a polymeric matrix and 0.1-15 wt. % of metal oxide particles, wherein the polymeric matrix has pores, the metal oxide particles are uniformly distributed throughout the pores, and the metal oxide particles have a specific surface area of about 25 m$^2$/g to about 450 m$^2$/g, (b) applying a chemical-mechanical polishing composition to the polishing layer of the polishing pad, (c) contacting the polishing layer of the polishing pad with a substrate, and (d) moving the polishing pad with respect to the substrate so as to abrade at least a portion of the substrate and thereby polish the substrate.

DETAILED DESCRIPTION OF THE INVENTION

The invention provides a chemical-mechanical polishing pad comprising a polymeric matrix and 0.1-15 wt. % of metal oxide particles, wherein the polymeric matrix has pores, the metal oxide particles are uniformly distributed throughout the pores, and the metal oxide particles have a specific surface area of about 25 m$^2$/g to 450 m$^2$/g.

The polymeric matrix can comprise, consist essentially of, or consist of any suitable polymeric material, typically a thermoplastic polymer or a thermoset polymer. Preferably the polymeric material is a thermoplastic polymer or a thermoset polymer selected from the group consisting of thermoplastic elastomers, thermoplastic polyurethanes, polyolefins, polycarbonates, polyvinylalcohols, nylons, elastomeric rubbers, styrenic polymers, polyaromatics, fluoropolymers, polyimides, cross-linked polyurethanes, cross-linked polyolefins, polyethers, polyesters, polyacrylates, elastomeric polyethylenes, polytetrafluoroethylenes, polyethyleneteraphthalates, polyimides, polyaramides, polyarylenes, polystyrenes, polymethylmethacrylates, copolymers and block copolymers thereof, and mixtures and blends thereof. Most preferably the polymeric material is a thermoplastic polyurethane (TPU).

The polishing pad can have any suitable mechanical properties. In one embodiment of the invention, the polishing pad has a low glass transition temperature. The glass transition temperature (Tg) of an amorphous solid is the temperature below which the solid exists in a glassy state where only vibrational motion is present, whereas above this temperature, individual molecular segments are able to move relative to each other in what is sometimes termed the "rubbery state" (see e.g., Daniel B. Miracle and Steven L. Donaldson, ASM Handbook, Volume 21: "Composites; Epoxy Resins," 2001, p. 78).

Lowering the glass transition temperature of the polishing pad creates a pad whose stiffness changes very little in the normal polishing temperature range of between 20° C. and 100° C. Thus changes in temperature have minimal effect on the physical properties of the polishing pad. The polishing pad of the invention can have a glass transition temperature of about +10° C. or less, e.g., about +5° C. or less, or about 0° C. or less. Alternatively, or in addition, the polishing pad can have a glass transition temperature of about −30° C. or more, e.g., about −20° C. or more, or about −10° C. or more. Thus, the polishing pad can have a glass transition temperature bounded by any two of the aforementioned end points. For example, the polishing pad can have a glass transition temperature of about −30° C. to about +10° C., or about −10° C. to about +5° C.

In another embodiment of the invention the polishing pad has a low elastic modulus (E). Elastic modulus is the mathematical description of an object or substance's tendency to be deformed elastically (i.e., non-permanently) when a force is applied to it. The elastic modulus of an object is defined as the slope of its stress-strain curve in the elastic deformation region: $\lambda$=stress/strain, where $\lambda$ (lambda) is the elastic modulus; stress is the force causing the deformation divided by the area to which the force is applied; and strain is the ratio of the change caused by the stress to the original state of the object. A polishing pad with a low elastic modulus is more flexible relative to an otherwise similar polishing pad having a higher elastic modulus.

The polishing pad can have an elastic modulus of about 100 MPa or less at 30° C., e.g., about 90 MPa or less at 30° C., about 80 MPa or less at 30° C., about 70 MPa or less at 30° C., about 60 MPa or less at 30° C., about 50 MPa or less at 30° C., or about 40 MPa or less at 30° C. Alternatively, or in addition, the polishing pad can have an elastic modulus of about 20 MPa or more at 30° C., e.g., about 30 MPa or more at 30° C., about 40 MPa or more at 30° C., about 50 MPa or more at 30° C., about 60 MPa or more at 30° C., about 70 MPa or more at 30° C., about 80 MPa or more at 30° C., or about 90 MPa or more at 30° C. Thus, the polishing pad can have an elastic modulus bounded by any two of the aforementioned endpoints. For example, the polishing pad can have an elastic modulus of about 30 MPa to about 50 MPa at 30° C., or about 50 MPa to about 70 MPa at 30° C. Most preferably, the polishing pad has an elastic modulus of about 30 MPa to about 100 MPa at 30° C.

In yet another embodiment, the polishing pad is relatively soft. An instrument that is typically used to measure hardness is the durometer made by Shore Instrument Company (see, e.g., Charles A. Harper, Edward M. Petrie, Plastics Materials and Processes: A Concise Encyclopedia, 2003, p. 247). Shore hardness values are scale numbers resulting from the indentation of a plastic material with a defined steel rod. ASTM D2240 describes Shore hardness measurements. The Shore A scale typically is used for softer polymeric materials. On the Shore A scale, 0 is soft, and 100 is hard. The Shore D scale typically is used for harder polymeric materials. Thermoset and thermoplastic materials typically fall between 40 and 90 on the Shore D scale.

The polishing pad can have a Shore A hardness of about 85 or less, e.g., about 80 or less, or about 75 or less, or about 70 or less. Alternatively, or in addition, the polishing pad can have a Shore A hardness of about 65 or more, e.g., about 70 or more, about 75 or more, or about 80 or more. Thus, the polishing pad can have a Shore A hardness bounded by any two of the aforementioned endpoints. For example, the polishing pad can have a Shore A hardness of about 65 to about 85, or about 70 to about 80. Most preferably, the polishing pad has a Shore A hardness measurement of about 65 to about 85.

The polishing pad can have a Shore D hardness of about 30 or less, e.g., about 20 or less. Alternatively, or in addition, the polishing pad can have a Shore D hardness of about 10 or more, e.g., about 20 or more. Thus, the polishing pad can have a Shore D hardness bounded by any of the aforementioned endpoints. For example, the polishing pad can have a Shore D hardness of about 10 to about 30, or about 15 to about 25. Most preferably, the polishing pad has a Shore D Hardness of about 10 to about 30.

In another embodiment, the polishing pad is hydrophilic. The hydrophilicity of a surface can be determined by measuring the water contact angle. The water contact angle is the angle at which a water interface meets the solid surface. A substance that is highly hydrophobic is characterized by a high water contact angle, e.g., from about 90° to about 180°. A surface that is highly hydrophilic is characterized by a low water contact angle, e.g. from about 0° to about 90°.

The polishing pad can have a water contact angle of 20° or more in 15 min, e.g., 30° or more in 15 min, 40° or more in 15 min, 50° or more in 15 min, or 60° or more in 15 min. Alternatively, or in addition, the polishing pad can have a water contact angle of 70° or less in 15 min, e.g., 60° or less in 15 min, 50° or less in 15 min, 40° or less in 15 min, or 30° or less in 15 min. Thus, the polishing pad can have a water contact angle bounded by any two of the aforementioned endpoints. For example, the polishing pad can have a water contact angle of 20°-70° in 15 min, 30°-60° in 15 min, or 40°-50° in 15 min. Most preferably, the polishing pad will have a water contact angle of 20°-70° in 15 min.

It is believed that the hydrophilic quality of the polishing pad leads to increased slurry flow across and within the polishing pad, thus enhancing the durability and uniformity of polishing of the pad. Without intending to be bound by any particular theory, it is believed that the addition of metal oxide particles to the polymeric matrix renders the polishing pad of the invention more hydrophilic.

The metal oxide particles that are uniformly distributed throughout the pores of the polymeric matrix can be of any suitable dimension (e.g., diameter, length, or width) or shape (e.g., spherical or oblong) and can be present in the polishing pad in any suitable amount. The metal oxide particles can have any suitable specific surface area. For example, the specific surface area of the metal oxide particles can about 25 $m^2/g$ or more, e.g., about 50 $m^2/g$ or more, about 100 $m^2/g$ or more, about 150 $m^2/g$ or more, about 200 $m^2/g$ or more, about 250 $m^2/g$ or more, about 300 $m^2/g$ or more, about 350 $m^2/g$ or more, or about 400 $m^2/g$ or more. Alternatively, or in addition, the metal oxide particles can have a specific surface area of about 450 $m^2/g$ or less, e.g., about 400 $m^2/g$ or less, about 350 $m^2/g$ or less, about 300 $m^2/g$ or less, about 250 $m^2/g$ or less, about 200 $m^2/g$ or less, about 150 $m^2/g$ or less, about 100 $m^2/g$ or less, or about 50 $m^2/g$ or less. Thus, the metal oxide particles can have a specific surface area bounded by any two of the aforementioned endpoints. For example, the metal oxide particles can have a specific surface area of about 25-450 $m^2/g$, about 50-400 $m^2/g$, about 100-350 $m^2/g$, about 150-300 $m^2/g$, about 200-250 $m^2/g$. Most preferably, the particle specific surface area is from about 25 $m^2/g$ to about 450 $m^2/g$.

The metal oxide particles can comprise, consist essentially of, or consist of any suitable metal oxide. For example, the metal oxide can be silica, alumina, titania, ceria, zirconia, germania, magnesia, co-formed products thereof, and combinations thereof. Preferably, the metal oxide particles are silica particles. The metal oxide particles can be of any suitable type and/or physical configuration, such as fumed metal oxides particles, precipitated metal oxide particles, condensation-polymerized metal oxide particles, etc. Preferably, the metal oxide particles are fumed metal oxide particles, especially fumed silica particles.

The polishing pad comprises a polymeric matrix having pores. The term "pore" describes void spaces within the polymeric matrix that are at least partially bounded solely by the polymeric material. In addition, the term "pore" describes both open and closed-celled pores. The polishing pad can have any suitable average pore size. For example, the polishing pad can have an average pore size of about 150 µm or less, e.g., about 140 µm or less, about 130 µm or less, about 120 µm or less, about 110 µm or less, about 100 µm or less, about 90 µm or less, about 80 µm or less, about 70 µm or less, or about 60 µm or less. Alternatively, or in addition, the polishing pad can have an average pore size of about 50 µm or more, e.g., about 60 µm or more, about 70 µm or more, about 80 µm or more, about 90 µm or more, about 100 µm or more, about 110 µm or more, about 120 µm or more, about 130 µm or more, or about 140 µm or more. Thus, the polishing pad can have an average pore size bounded by any two of the above endpoints. For example, the polishing pad can have an average pore size of about 50-150 µm, about 60-140 µm, about 70-130 µm, about 80-120 µm, or about 90-110 µm. Most preferably, the polishing pad has an average pore size of about 50 µm to about 150 µm.

The polishing pad can have any suitable pore size distribution. Typically about 20% or more (e.g., about 30% or more, about 40% or more, or about 50% or more) of the pores in the polishing pad (i.e., cells) have a pore size distribution of about ±100 µm or less (e.g., about ±50 µm or less) of the average pore size. Preferably the pad has a highly uniform distribution of pore sizes. For example, about 75% or more (e.g., about 80% or more, or about 85% or more) of the pores in the polishing pad have a pore size distribution of about ±20 µm or less (e.g., about ±10 µm or less, about ±5 µm or less, or about ±2 µm or less) of the average pore size. In other words, about 75% or more (e.g., about 80% or more, or about 85% or more) of the pores in the polishing pad have a pore size within about 20 µm or less (e.g., about ±10 µm or less, about ±5 µm or less, or about ±2 µm or less) of the average pore size. More preferably, about 90% or more (e.g., about 93% or more, about 95% or more, or about 97% or more) of the pores in the polishing pad have a pore size distribution of about ±20 µm or less (e.g., about ±10 µm or less, about ±5 µm or less, or about ±2 µm or less) of the average pore size.

Additionally, the polishing pad can have a multi-modal distribution of pores. The term "multi-modal" means that the porous region has a pore size distribution comprising at least 2 or more (e.g., about 3 or more, about 5 or more, or even about 10 or more) pore size maxima. Typically the number of pore size maxima is about 20 or less (e.g., about 15 or less). A pore size maximum is defined as a peak in the pore size distribution whose area comprises about 5% or more by number of the total number of pores. Preferably, the pore size distribution is bimodal (i.e., has two pore size maxima).

The multi-modal pore size distribution can have pore size maxima at any suitable pore size values. For example, the multi-modal pore size distribution can have a first pore size maximum of about 150 µm or less (e.g., about 120 µm or less, about 100 µm or less, or about 80 µm or less) and a second pore size maximum of about 50 µm or more (e.g., about 60 µm or more, about 80 µm or more, or about 100 µm or more).

Typically the polishing pad comprises predominantly closed cells (i.e., pores); however, the polishing pad alternatively or additionally can also comprise open cells. The void volume, which results from the open and closed cells in the polishing pad, can comprise any suitable value. The polishing pad can have a void volume of about 5% or more, e.g., about 10% or more, about 20% or more, about 30% or more, about 40% or more, about 50% or more, about 60% or more, or about 70% or more. Alternatively, or in addition, the polishing pad can have a void volume of about 80% or less, e.g., about 70% or less, about 60% or less, about 50% or less, about 40% or less, about 30% or less, about 20% or less, or about 10% or less. Thus, the polishing pad of the invention can have a void volume bounded by any two of the above endpoints. For example, the polishing pad of the invention can have a void volume of about 5% to about 80%, about 10% to about 70%, about 20% to about 60%, or about 30% to about 50%. Most preferably, the void volume of the polishing pad is about 20% to about 60%.

The polishing pad can have any suitable shape and dimensions. Typically, the polishing pad will be circular in shape (as is used in rotary polishing tools) or will be produced as a looped linear belt (as is used in linear polishing tools).

The polishing pad has a polishing surface which optionally further comprises grooves, channels, and/or perforations which facilitate the lateral transport of polishing compositions across the surface of the polishing pad. Such grooves, channels, or perforations can be in any suitable pattern and can have any suitable depth and width. The polishing pad can have two or more different groove patterns, for example a combination of large grooves and small grooves as described in U.S. Pat. No. 5,489,233. The grooves can be in the form of slanted grooves, concentric grooves, spiral or circular grooves, XY crosshatch pattern, and can be continuous or non-continuous in connectivity. Preferably, the polishing pad of the invention comprises at least grooves in an XY crosshatch pattern produced by standard pad conditioning methods.

The polishing pad can be prepared by any suitable technique. The polymeric matrix can comprise a pre-formed polymer resin; however, the polymer resin also can be formed in situ according to any suitable method, many of which are known in the art (see, for example, *Szycher's Handbook of Polyurethanes*, CRC Press: New York, 1999, Chapter 3). For example, thermoplastic polyurethane can be formed in situ by the reaction of urethane prepolymers, such as isocyanate, di-isocyanate, and tri-isocyanate prepolymers, with a prepolymer containing an isocyanate reactive moiety. Suitable isocyanate reactive moieties include amines and polyols. The metal oxide particles can be incorporated into the polymeric matrix by any means. The particles preferably are blended with the polymer resin before being formed into a polishing substrate.

The polishing pad can be used alone or optionally can be used as one layer of a multi-layer stacked polishing pad. For example, the polishing pad can be used in combination with a subpad. The subpad can be any suitable subpad. Suitable subpads include polyurethane foam subpads (e.g., foam subpads from Rogers Corporation), impregnated felt subpads, microporous polyurethane subpads, or sintered urethane subpads. The subpad typically is softer than the polishing pad and therefore is more compressible and has a lower Shore hardness value than the polishing pad. For example, the subpad can have a Shore A hardness of about 35 to about 50. In some embodiments, the subpad is harder, is less compressible, and has a higher Shore hardness than the polishing pad. The subpad optionally comprises grooves, channels, hollow sections, windows, apertures, and the like. When the polishing pad is used in combination with a subpad, typically there is an intermediate backing layer, such as a polyethyleneterephthalate film, coextensive with and in between the polishing pad and the subpad. Alternatively, the polishing pad can be used as a subpad in conjunction with a conventional polishing pad.

The polishing pad is particularly suited for use in conjunction with a chemical-mechanical polishing (CMP) apparatus. Typically, the apparatus comprises a platen, which, when in use, is in motion and has a velocity that results from orbital, linear, or circular motion, a polishing pad in contact with the platen and moving with the platen when in motion, and a carrier that holds a substrate to be polished by contacting and moving relative to the surface of the polishing pad intended to contact a substrate to be polished. The polishing of the substrate takes place by the substrate being placed in contact with the polishing pad and then the polishing pad moving relative to the substrate, typically with a polishing composition therebetween, so as to abrade at least a portion of the substrate to polish the substrate. The CMP apparatus can be any suitable CMP apparatus, many of which are known in the art. The polishing pad also can be used with linear polishing tools.

The polishing pad is typically used in conjunction with a polishing composition or slurry. The polishing composition can be any suitable polishing composition, many of which are known in the art. Preferably, the polishing pad of the invention can be used in conjunction with a commercially available polishing composition, for example, Semi-Sperse® 25-E Dielectric CMP Slurry (Cabot Microelectronics, Aurora, Ill.). Semi-Sperse® 25-E Dielectric CMP Slurry is a colloidally stable polishing composition containing fumed silica abrasive stabilized by potassium hydroxide. Most preferably, the polishing pad of the invention is used in conjunction with the commercially available polishing composition, Semi-Sperse® 25-E Dielectric CMP Slurry that is concentrated and which, prior to polishing, is diluted by adding 1 part of water to 1 part of composition at point of use, such that there is 12 wt. % solid at point-of-use (hereinafter "SS25EY").

The polishing pad is suitable for use in polishing many types of substrates and substrate materials. For example, the polishing pad can be used to polish a variety of substrates including memory storage devices, semiconductor substrates, and glass substrates. Suitable substrates for polishing with the polishing pad include memory disks, rigid disks, magnetic heads, MEMS devices, semiconductor wafers, field emission displays, and other microelectronic substrates, especially substrates comprising insulating layers (e.g., silicon dioxide, silicon nitride, or low dielectric materials) and/or metal-containing layers (e.g., copper, tantalum, tungsten, aluminum, nickel, titanium, platinum, ruthenium, rhodium, iridium, or other noble metals).

EXAMPLES

The following examples further illustrate the invention but, of course, should not be construed as in any way limiting its scope.

Example 1

This example demonstrates the enhanced polishing rate exhibited by the polishing pad of the invention.

Similar substrates were polished using three different polishing pads identified as polishing pads 1A-1C. Polishing pad 1A was a polishing pad of the invention, while polishing pad 1B was a polishing pad, similar to polishing pad 1A except for the absence of metal oxide particles. Polishing pad 1C was a commercially available polishing pad, namely an EPIC™ D100 polishing pad (Cabot Microelectronics, Aurora, Ill.), which contained no metal particles. The physical properties of the respective polishing pads are set forth in Table 1A.

TABLE 1A

| Pad | Polymeric Matrix Material | Silica (wt. %) | Resin Hardness | Hardness Shore A | Hardness Shore D | Elastic Modulus @ 30° C. | Tg (° C.) |
|---|---|---|---|---|---|---|---|
| 1A (invention) | TPU | 6 | 85 (Shore A) | 72 | 22 | 42 | 3 |
| 1B (comparative) | TPU | 0 | 85 (Shore A) | 82 | 22 | 25 | −8 |
| 1C (commercial pad) | TPU | 0 | 72 (Shore D) | 96 | 68 | 475 | 50 |

Each of the three polishing pads was used to polish a series of 100 mm thermal oxide (TEOS) wafers under similar polishing conditions at the rate of one TEOS wafer per minute for 180 total minutes. The polishing was carried out on a Logitech polisher using 38.1 cm (15 inch) diameter circular polishing pads with XY grooving and a commercially available polishing composition, SS25EY. The polishing was carried out under the following conditions: 41.4 kPa (6 psi) down force, 120 rpm platen speed, 115 rpm carrier speed, and 150 ml/min slurry flow rate. There was no sweep for carrier.

The substrate removal rate for 12 of the 180 TEOS wafers was measured for each of polishing pads 1A, 1B, and 1C, such that the substrate removal rate was determined at 12 points in time over the course of the 180 minutes of total polishing time. The resulting data is plotted in FIG. 1. The average of the substrate removal rates, utilizing the substrate removal rates measured for the aforementioned 12 selected TEOS wafers for each of polishing pads 1A, 1B, and 1C, are set forth in Table 1B.

TABLE 1B

| Pad | Average TEOS Removal Rate (Å/min) | TEOS Removal Rate Change After 180 min Polishing |
|---|---|---|
| 1A (invention) | 3148 | −0.8% |
| 1B (comparative) | 2022 | −30% |
| 1C (commercial) | 2053 | −0.6% |

Figure 1:
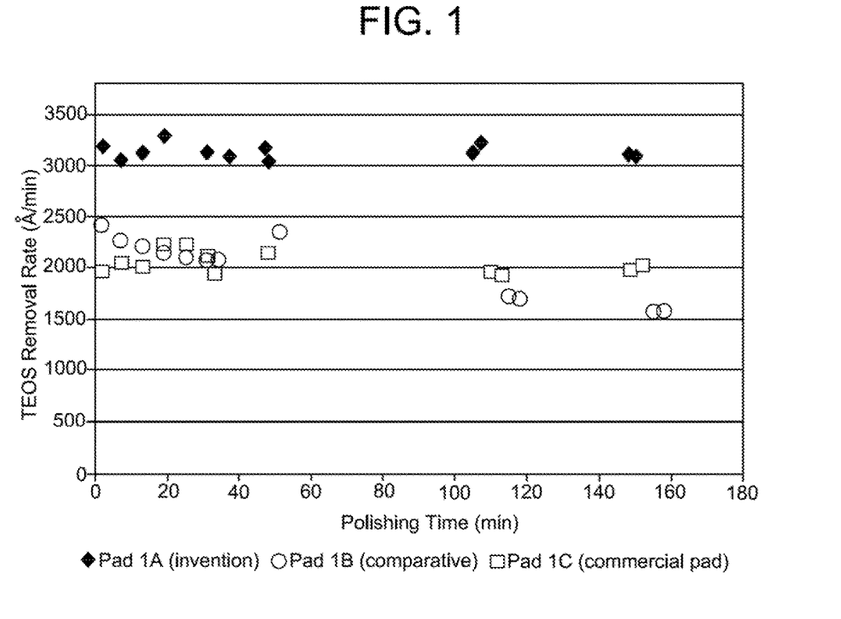
FIG. 1 is a graph of the average thermal oxide (TEOS) removal rate (Å/min) exhibited by inventive and comparative polishing pads over 180 minutes of total polishing time as described in Example 1.
Figure 2A:
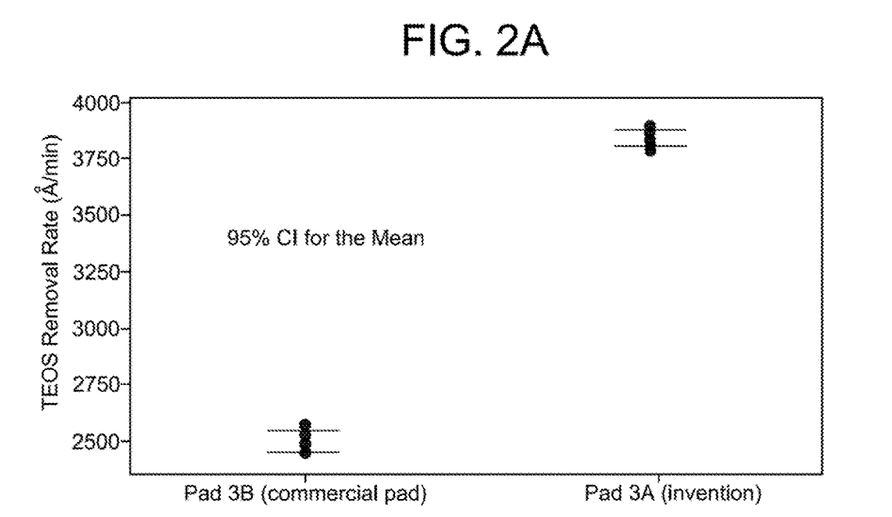
FIG. 2A is a graph of the TEOS removal rate (Å/min) exhibited by inventive and comparative polishing pads as described in Example 3.
Figure 2B:
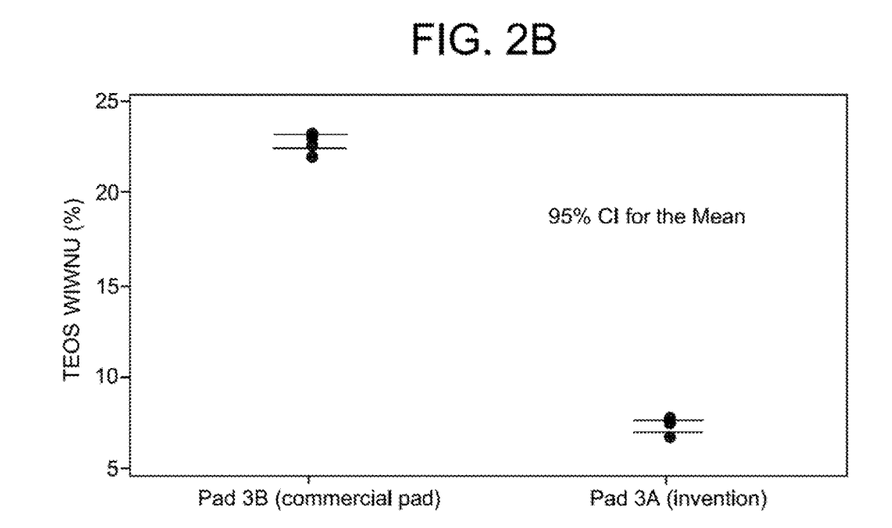
FIG. 2B is a graph of the within wafer nonuniformity (WIWNU) (%) exhibited by inventive and comparative polishing pads as described in Example 3.
Figure 2C:
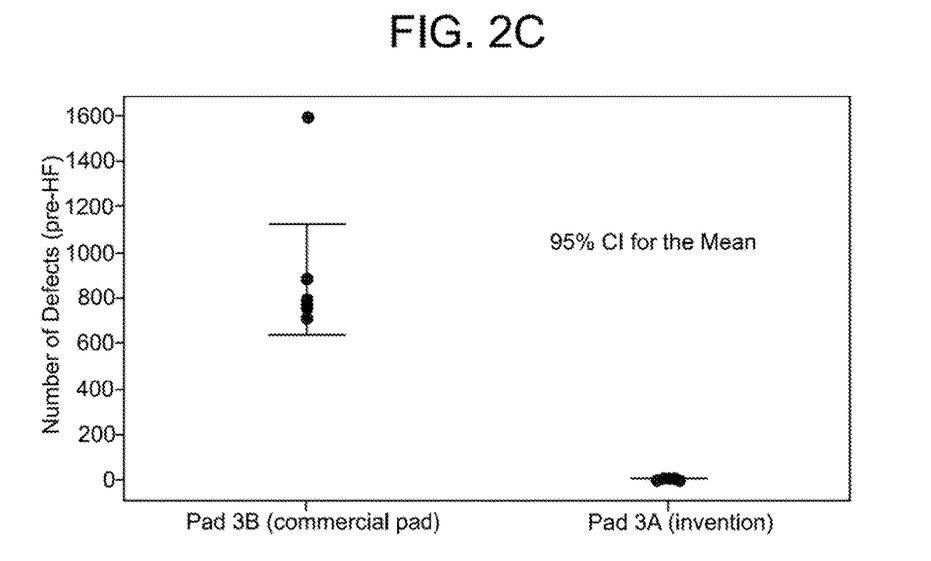
FIG. 2C is a graph of the number of defects (prior to an HF wash) on wafers polished by inventive and comparative polishing pads as described in Example 3.
Figure 2D:
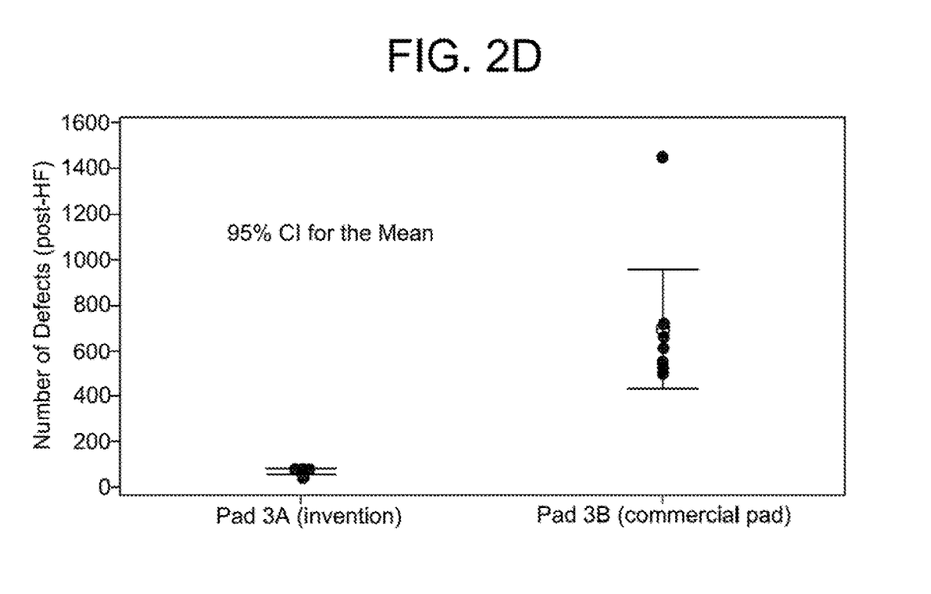
FIG. 2D is a graph of the number of defects (after an HF wash) on wafers polished by inventive and comparative polishing pads as described in Example 3.

As is apparent from the results set forth in Table 1B and plotted in FIG. 1, the polishing pad of the invention exhibited a higher average TEOS removal rate as compared to comparative polishing pad 1B, which is similar to inventive polishing pad 1A except for the absence of metal oxide particles. Additionally, inventive polishing pad 1A exhibited a higher average TEOS removal rate as compared to commercial polishing pad 1C, which had a higher Shore D hardness measurement, elastic modulus, and glass transition temperature than inventive polishing pad 1A.

Example 2

This example demonstrates the effect of the polishing pad's physical properties (specifically hardness, elastic modulus, void volume, glass transition temperature, and metal oxide particle content) on TEOS and BPSG removal rates compared to other pads with different physical properties.

Similar substrates were polished using six different polishing pads identified as polishing pads 2A, 2B, 2C, 2D, 2E, and 2F. Polishing pads 2B and 2D were polishing pads of the invention. Polishing pads 2A and 2C were composed of the same resin as pads 2B and 2D respectively, but contained no metal oxide particles. Polishing pad 2E was a commercially available polishing pad, namely an EPIC™ D100 polishing pad (Cabot Microelectronics, Aurora, Ill.) and contained no metal particles. Pad 2F had similar physical properties to polishing pad 2D, but contained no metal oxide particles.

Each of the six polishing pads was used to polish TEOS and BPSG wafers. The polishing was carried out on a Logitech polisher using 38.1 cm (15 inch) diameter circular polishing pads with XY grooving and a commercially available polishing composition, SS25EY. The polishing was carried out under the following conditions: 41.4 kPa (6 psi) down force, 120 rpm platen speed, 115 rpm carrier speed, and 150 ml/min slurry flow rate. There was no sweep for carrier. Table 2 sets out the properties of the six polishing pads and the average TEOS and BPSG removal rates for each pad. The TEOS removal rate is the average of 12 wafers polished by each of polishing pads 2A-2F. The BPSG removal rate is the average of two wafers polished by each of polishing pads 2A-2F.

TABLE 2

| | Hardness Shore A | Hardness Shore D | Elastic Modulus @ 30° C. | Void Volume (%) | Tg (° C.) | Silica (wt. %) | TEOS RR (Å/min) | BPSG RR (Å/min) |
|---|---|---|---|---|---|---|---|---|
| 2A (comparative) | 85 | 30 | 27 | 8 | −16 | 0 | 2209 | 5806 |
| 2B (invention) | 66 | 15 | 20 | 40 | −24 | 6 | 2468 | 7386 |

TABLE 2-continued

|  | Hardness | | Elastic Modulus | Void Volume | Tg | Silica | TEOS RR | BPSG RR |
|---|---|---|---|---|---|---|---|---|
|  | Shore A | Shore D | @ 30° C. | (%) | (° C.) | (wt. %) | (Å/min) | (Å/min) |
| 2C (comparative) | 82 | 22 | 25 | 9 | −8 | 0 | 2022 | 4399 |
| 2D (invention) | 72 | 23 | 42 | 40 | 3 | 6 | 3148 | 7737 |
| 2E (commercial) | 96 | 68 | 475 | 18 | 50 | 0 | 2053 | 4963 |
| 2F (comparative) | 79 | 26 | 52 | 25 | 6 | 0 | 2621 | 6210 |

As is apparent from the results set forth in Table 2, the presence of 6 wt. % silica particles in polishing pads 2B and 2D of the invention resulted in an increase in average TEOS and BPSG removal rates as compared to polishing pads 2A and 2C, which were similar except for the absence of silica particles, and commercial polishing pad 2E, which had a much higher Shore D hardness, elastic modulus, and glass transition temperature. In addition, polishing pad 2D of the invention had higher TEOS and BPSG average removal rates than comparative polishing pad 2F, which had similar Shore A and D hardness values, elastic modulus, and glass transition temperature, but contained no metal oxide particles.

Example 3

This example demonstrates the increased oxide removal rate, reduced defectivity, and reduced within wafer nonuniformity (WIWNU) achieved by the polishing pad of the invention during polishing compared to a commercially available polishing pad.

Similar substrates were polished using two different polishing pads identified as pads 3A and 3B. Polishing pad 3A was a polishing pad of the invention, while polishing pad 3B was a commercially available pad, namely an EPIC™ D100 polishing pad (Cabot Microelectronics, Aurora, Ill.), which does not contain any metal oxide particles.

Each of the two polishing pads was used to polish TEOS wafers. The polishing was carried out on a Mirra polisher using 38.1 cm (15 inches) diameter circular polishing pads with XY grooving and a commercially available polishing composition, SS25EY. The polishing was carried out under the following conditions: 41.4 kPa (6 psi) down force, 120 rpm platen speed, 85 rpm carrier speed, and 175 ml/min slurry flow rate. There was no sweep for carrier. The substrate removal rates, WIWNU, and the number of defects (both before and after a hydrofluoric acid wash) were determined for 8 wafers polished by each of the two polishing pads, and the average results are set forth in Table 3 and plotted in the graphs of FIGS. 2A-2D.

TABLE 3

|  | TEOS Removal Rate (Å/min) | | WIWNIU (%) | | Number of Defects | | | |
|---|---|---|---|---|---|---|---|---|
|  | | | | | Pre-HF Wash | | Post-HF Wash | |
|  | mean | stdev | mean | stdev | mean | stdev | mean | stdev |
| 3A (invention) | 3853 | 41 | 7.5 | 0.3 | 15 | 3 | 69 | 15 |
| 3B (commercial pad) | 2503 | 48 | 22.8 | 0.4 | 782 | 54 | 697 | 64 |

These results show that, surprisingly, inventive polishing pad 3A exhibited a higher TEOS removal rate, reduced WIWNU, and reduced defectivity than commercial polishing pad 3B despite having a lower elastic modulus, Shore D hardness, and glass transition temperature.

Example 4

This example demonstrates the effect of the polishing pad's physical properties (specifically hardness, elastic modulus, void volume, glass transition temperature and metal oxide particle content) on TEOS removal rates compared to other polishing pads with different physical properties.

Similar substrates were polished using four different polishing pads identified as polishing pads 4A, 4B, 4C, and 4D. Polishing pads 4B and 4D were polishing pads of the invention. Polishing pads 4A and 4C were composed of the same resin as pads 4B and 4D respectively, but contained no metal oxide particles.

Each of the four polishing pads was used to polish TEOS wafers. The polishing was carried out on Mirra polisher using 50.8 cm (20 inches) diameter circular pads with concentric grooving and a commercially available polishing composition, SS25EY. The polishing was carried out under the following conditions: 6 psi down force, 120 rpm platen speed, 85 rpm carrier speed, and 150 ml/min slurry flow rate. Table 4 sets out the properties of the four polishing pads and the average TEOS removal rates for each polishing pad. For pads 4A, 4B, and 4D, the TEOS removal rate is the average of 2 wafers polished by each of the polishing pads. For polishing pad 4C, the TEOS removal rate is the average of 5 wafers polished by the polishing pad.

TABLE 4

|  | Hardness (Shore A) | Modulus @ 30° C. | Void Volume (%) | Tg (° C.) | Silica (wt. %) | TEOS RR (Å/min) |
|---|---|---|---|---|---|---|
| 4A (comparative) | 80A | 66 | 35% | 17 | 0 | 4162 |
| 4B (invention) | 80A | 82 | 43% | 14 | 1 | 4857 |
| 4C (comparative) | 73A | 65 | 43% | 20 | 0 | 3573 |
| 4D (invention) | 73A | 67 | 43% | 18 | 1 | 4423 |

As is apparent from the results set forth in Table 4, the presence of 1 wt. % silica particles in polishing pads 4B and 4D of the invention resulted in an increase in the average TEOS removal rate as compared to polishing pads 4A and 4C, which were similar except for the absence of silica particles. In addition, polishing pad 4D of the invention had a higher TEOS average removal rate than comparative polishing pad 4C, which had a similar Shore A hardness value, elastic modulus, glass transition temperature, and void volume, but contained no metal oxide particles.

All references, including publications, patent applications, and patents, cited herein are hereby incorporated by reference to the same, extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements and all possible variations thereof is encompassed by the invention unless otherwise indicated herein or otherwise clearly contradicted by context.

The invention claimed is:

1. A chemical-mechanical polishing pad comprising a polymeric matrix and 0.1-15 wt. % of metal oxide particles, wherein the pad has pores, the metal oxide particles are uniformly distributed throughout the pores, and the metal oxide particles have a specific surface area of about 25 $m^2/g$ to about 450 $m^2/g$, wherein the polymeric matrix comprises thermoplastic polyurethane.

2. The polishing pad of claim 1, wherein the metal oxide particles comprise silica particles.

3. The polishing pad of claim 2, wherein the metal oxide particles comprise fumed silica particles.

4. The polishing pad of claim 1, wherein the pad has a Shore A hardness measurement of about 65 to about 85.

5. The polishing pad of claim 1, wherein the pad has a void volume of about 20% to about 60%.

6. The polishing pad of claim 1, wherein the average pore size is about 50 µm to about 150 µm.

7. The polishing pad of claim 1, wherein the pad has a glass transition temperature Tg of about −30° C. to about +10° C.

8. The polishing pad of claim 1, wherein the pad has an elastic modulus E of about 30 MPa to about 100 MPa at 30° C.

9. The polishing pad of claim 1, wherein the pad has a water contact angle of about 20° to about 70° in 15 min.

10. The polishing pad of claim 1, wherein the metal oxide particles comprise fumed silica particles, the polymeric matrix comprises thermoplastic polyurethane, and where the pad has a void volume of about 20% to about 60%, an average pore size of about 50 µm to about 150 µm, a Shore A hardness measurement of about 65 to about 85, a glass transition temperature of about −30° C. to about +10° C., an elastic modulus E of about 30 MPa to about 100 MPa at 30° C., and a water contact angle of about 20° to about 70° in 15 min.

11. A method of polishing a substrate, the method comprising:
(i) providing a polishing pad having a polishing layer comprised of a polymeric matrix and 0.1-15 wt % of metal oxide particles, wherein the pad has pores, the metal oxide particles are uniformly distributed throughout the pores, the metal oxide particles have a specific surface area of about 25 $m^2/g$ to about 450 $m^2/g$, and the polymeric matrix comprises thermoplastic polyurethane,
(ii) applying a chemical-mechanical polishing composition to the polishing layer of the polishing pad,
(iii) contacting the polishing layer of the polishing pad with a substrate, and
(iv) moving the polishing pad with respect to the substrate so as to abrade at least a portion of the substrate and thereby polish the substrate.

12. The method of claim 11, wherein the metal oxide particles comprise silica particles.

13. The method of claim 12, wherein the metal oxide particles comprise fumed silica particles.

14. The method of claim 11, wherein the pad has a Shore A hardness measurement of about 65 to about 85.

15. The method of claim 11, wherein the pad has a void volume of about 20% to about 60%.

16. The method of claim 11, wherein the average pore size is about 50 µm to about 150 µm.

17. The method of claim 11, wherein the pad has a transition temperature Tg of about −30° C. to about +10° C.

18. The method of claim 11, wherein the pad has an elastic modulus E of about 30 MPa to about 100 MPa at 30° C.

19. The method of claim 11, wherein the pad has a water contact angle of about 20° to about 70° in 15 min.

20. The method of claim 11, wherein the metal oxide particles comprise fumed silica particles, the polymeric matrix comprises thermoplastic polyurethane, and where the pad has a void volume of about 20% to about 60%, an average pore size of about 50 µm to about 150 µm, a Shore A hardness measurement of about 65 µm to about 85 µm, a glass transition temperature of about −30° C. to about +10° C., an elastic modulus E of about 30 MPa to about 100 MPa at 30° C., and a water contact angle of about 20° to about 70° in 15 min.

* * * * *